United States Patent [19]

Feuer et al.

[11] 4,163,746

[45] Aug. 7, 1979

[54] METABOLIC 5-METHYL-ISOFLAVONE-DERIVATIVES, PROCESS FOR THE PREPARATION THEREOF AND COMPOSITIONS CONTAINING THE SAME

[75] Inventors: László Feuer; Lóránd Farkas; Mihály Nógrádi; Borbáia Vermes; Ágnes Gottsegen; András Wolfner, all of Budapest, Hungary

[73] Assignee: Chinoin Gyogyszer es Vegyeszeti Termekek Gyara Rt., Budapest, Hungary

[21] Appl. No.: 845,680

[22] Filed: Oct. 26, 1977

Related U.S. Application Data

[63] Continuation-in-part of Ser. No. 486,513, Jul. 8, 1974, abandoned.

[30] Foreign Application Priority Data

Jul. 9, 1973 [HU] Hungary ............................. CI 1396

[51] Int. Cl.$^2$ .......................................... C07D 311/02
[52] U.S. Cl. ................................. 260/345.2; 424/283
[58] Field of Search ..................................... 260/345.2

[56] References Cited

U.S. PATENT DOCUMENTS

| 3,352,754 | 11/1967 | Gazave | 260/345.2 |
| 3,833,730 | 9/1974 | Feuer et al. | 260/345.2 |

FOREIGN PATENT DOCUMENTS 2125245 12/1971 Fed. Rep. of Germany ........ 260/345.2

OTHER PUBLICATIONS

Moersch et al., J. Med. Chem., 10, 154, (1967).

*Primary Examiner*—Nicky Chan
*Attorney, Agent, or Firm*—Karl F. Ross

[57] ABSTRACT

Nonestrogenic 5-methyl-alkoxy-isoflavone, namely, 5-methyl-7-methoxy-isoflavone, 5-methyl-7-ethoxy-isoflavone, 5-methyl-7-isopropoxy-isoflavone, and 5-methyl-7-(2-hydroxy-ethoxy)-isoflavone are useful as weight-gain promoters in feeds from which the 7-methoxy and 7-ethoxy isoflavones have been excluded because of estrogenic effects. They are more effective than 7-isopropoxy-isoflavone as well.

5 Claims, No Drawings

METABOLIC 5-METHYL-ISOFLAVONE-DERIVATIVES, PROCESS FOR THE PREPARATION THEREOF AND COMPOSITIONS CONTAINING THE SAME

CROSS-REFERENCE TO RELATED APPLICATION

This application is a continuation-in-part of application Ser. No. 486,513 filed 8 July 1974, now abandoned.

This invention relates to 5-methyl-isoflavone derivatives suitable for use as or in animal feeds.

According to a feature of the present invention, there are provided new compounds of the formula I

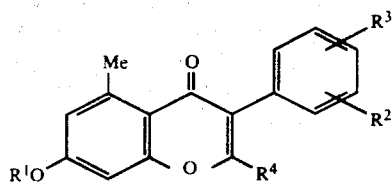

wherein
$R^1$ is hydrogen or substituted or unsubstituted alkyl or substituted or unsubstituted aralkyl;
$R^2$ and $R^3$ are each hydrogen, alkyl or alkoxy;
$R^4$ is hydrogen or alkyl.

Similar isoflavone-derivatives unsubstituted in position 5 are described in U.S. Pat. No. 3,864,362. These compounds possess useful metabolic properties.

If $R^1$ stand for substituted or unsubstituted alkyl, the alkyl may be a straight or branched chained alkyl group, having 1–20 carbon atoms. The substituent of the alkyl group may be preferably a hydroxy or $C_{1-16}$ alkoxy group (e.g. methyl, ethyl, isopropyl, hydroxyethyl, 2-methyl-propyl, 3-methyl-butyl, hexadecyl, etc.).

If $R^1$ is an optionally substituted aralkyl group, it contains preferably 7–9 carbon atoms (e.g. benzyl, beta-phenyl-ethyl).

$R^2$, $R^3$ and $R^4$ are preferably hydrogen.

Particularly preferred representatives of the compounds of the formula I are the following derivatives:
5-methyl-7-methoxy-isoflavone;
5-methyl-7-(2-hydroxy-ethoxy)-isoflavone;
5-methyl-7-ethoxy-isoflavone; and
5-methyl-7-isopropoxy-isoflavone.

The process for the preparation of compounds of the formula I comprises (a) reacting a ketone of the formula II

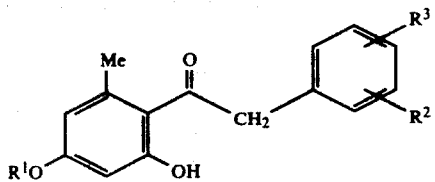

wherein $R^1$, $R^2$ and $R^3$ have the above-stated meanings with a trialkylorthoformiate in the presence of a basic catalyst; or (b) reacting a ketone of the formula II with hydrogen cyanide and/or a cyanide salt in the presence of a hydrogen halide; or (c) reacting a ketone of the formula II with an alkyl formiate in the presence of an alkali metal; or (d) reacting a ketone of the formula II with an alkyl-oxalyl-halide and subjecting the isoflavone ester thus obtained to saponification and/or decarboxylation; or (e) reacting a ketone of the formula II with an organic acid anhydride; or (f) dehydrating a 7-hydroxy-isoflavanone of the formula III

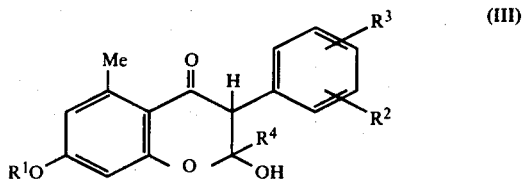

and, if desired, alkylating or aralkylating a compound of the formula I, wherein $R^1$ is hydrogen.

In carrying out variant (a) of the process, the preferred method is to react an appropriately substituted ketone with an orthoformic ester in an aprotic solvent of higher boiling point.

Pyridine, dimethyl formamide or diethyleneglycol dimethylether are used as solvents, while preferably piperidine, morpholine, pyrrolidine and other secondary amines serve as basic catalysts.

In carrying out variant (b), the preferred method is to react the ketones with hydrogen cyanide, in an aprotic solvent, in the presence of dry gaseous hydrochloric acid or of other hydrogen halides and Lewis acids. In this reaction, also aprotic solvents of non-basic nature, preferably diethylether or other dialkylethers, can be used. Zinc chloride or similarly acting Lewis acids may be used as catalysts. The reaction is carried out with hydrogen cyanide or with one of its appropriate salts, preferably with zinc cyanide. The mixture may be saturated with dry gaseous hydrogen chloride, and lastly, the formed substituted α-formimino-2-hydroxy-phenyl-benzyl-ketone hydrochlorides are decomposed by treatment with water.

In carrying out variant (c) of the process, ketones of the aforementioned formula II are reacted with alkyl formates in the presence of an alkali metal. A preferred method is to dissolve an appropriately substituted 2-hydroxy-phenyl-benzyl-ketone in ethyl formate, and adding the solution dropwise to powdered sodium metal, then decomposing the reaction mixture with water, and separating the formed isoflavone.

According to variant (d) of the process appropriately substituted 2-hydroxy-phenyl-benzyl-ketones are reacted with alkyl oxalyl halides. The formed 2-carbalkoxy-isoflavone derivative is converted, if desired, into an isoflavone derivative unsubstituted in position 2 by hydrolysis of the ester group followed by decarboxylation. This process is carried out preferably with methyl or ethyl oxalyl chloride in the presence of a basic acid-binding agent in an appropriate aprotic solvent (preferably pyridine or an other tertiary amine capable of binding acids).

According to variant (e) of the process, the appropriately substituted 2-hydroxy-phenyl-benzyl-ketone is reacted with organic acid anhydrides in the presence of a basic catalyst. The anhydrides of acetic, propionic or benzoic acids can be used as organic acid anhydrides. The anhydride is heated in the presence of the basic catalyst, preferably of the alkali metal salt of the acid component of the anhydride or of a tertiary amine, in the absence of solvents or in an aprotic solvent of higher boiling point such as pyridine or dimethyl formamide.

In carrying out of variant (f) of the process, 2-hydroxy-isoflavanones of the formula III are dehydrated by heating alone or in an acidic medium in a polar solvent. Compounds of the formula I, in which $R^1$ is hydrogen may be subjected to alkylation or aralkylation to provide compounds of the formula I, wherein $R^1$ is alkyl or aralkyl. The reaction may be carried out by methods known per se. Conventional alkylating agents (e.g. alkyl halides, such as methyl chloride, ethyl iodide, isopropyl bromide, etc. or dialkyl sulphates, e.g. diethyl sulphate) may be used. The reaction may be carried out preferably in the presence of an acid-binding agent (e.g. alkali carbonates, such as potassium carbonate). The reaction is preferably effected in an inert organic solvent, such as acetone or dimethylformamide.

The pharmaceutical compositions comprise, as the active ingredient, a compound of the formula I in admixture with suitable, inert carriers or diluents.

The compounds of the formula I are metabolic agents. Some of these compounds are of anabolic activity. These compounds increase calcium, phosphorous, potassium and nitrogen retention to a significant degree. Due to the above anabolic properties, the compounds are useful in the treatment of osteoporosis of gerontological and immobilation origin. An important advantage of these compounds over anabolic agents belonging to the sterane group is that they do not exhibit androgenic or liver damaging side effects. The decrease of the oxygen consumption of the tissues influences hypoxial or hypercapnial states advantageously in certain cardiological and pulmonological symptoms. The publication of Miklós Gábor, Naturwissenschaften No. 46,650 (1959) describes that isoflavones containing methoxy or hydroxy groups in 5,7,3' and/or 4' positions are estrogenic. The estrogenic activity of the following compounds was specifically disclosed:
Genistein: 5,7,4'-trihydroxyisoflavone;
daidzin: 7,4'-dihydroxyisoflavone;
biochanin: 5,7-dihydroxy-4'-methoxyisoflavone;
formomonetin: 7-hydroxy-4'-methoxyisoflavone;
pratensin: 5,7,3'-trihydroxy-4'-ethoxyisoflavone;
prunetin: 4',5-dihidroxy-7-methoxyisoflavone,
wherein the rings are numbered as follows:

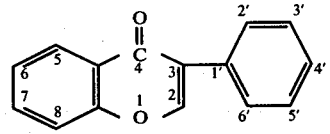

As anabolic agents devoid of side effects, the compounds of the invention are useful in human therapy as roborating agents. They can also be applied in pediatrics.

The following compounds of the formula I are particularly active as anabolic agents:
5-methyl-7-methoxy-isoflavone;
5-methyl-7-ethoxy-isoflavone;
5-methyl-7-(2-hydroxy-ethoxy)-isoflavone; and
5-methyl-7-isopropoxy-isoflavone.

The above compounds are useful as anorexigenic agents. A significant advantage of these compounds over known catabolic agents is that they do not exhibit a central stimulating effect. A further characteristic feature of these compounds is that they reduce the high blood cholesterol level and consequently may be used in the treatment of diseases, being in connection with cholesterinaemia (arteriosclerosis, diabetes, etc.).

The pharmaceutical compositions comprise a compound of the formula I and inert solid or liquid carriers. The compositions may be put up in solid (e.g. tablets, capsules, pills) or liquid (e.g. solution, emulsion, suspension) form. The composition contain conventional diluents or carriers (e.g. talc, magnesium stearate, calcium carbonate, starch, water) and optionally further additives (e.g. emulsifying, suspending, wetting agents, etc.). The compositions may also contain further biologically active components (anabolic, appetite-increasing, coronary dilatory agents, vitamin, agents acting on the hear function, etc.). The daily dosage of the compounds of the formula I may vary between wide ranges and depend on the particular conditions of application. A preferred oral dosage unit may be a tablet, pill or dragee, comprising 10–100 mg. of the active ingredient. Two or three tablets may be used a day. The above data are, however, merely of illustrative, rather than restricting character.

According to a still further feature of the present invention, there are provided feed additives, comprising at least one anabolic compound of the formula I as the active ingredient.

Particularly useful anabolic feed additives are the following compounds:
5-methyl-7-methoxy-isoflavone;
5-methyl-7ethoxy-isoflavone;
5-methyl-7-(2-hydroxy-ethoxy)-isoflavone; and
5-methyl-7-isopropoxy-isoflavone.

These compounds of the formula I produce a significant weight gain increase in domestic animals as compared to that of the control. It is of importance that the surplus of weight consists of meat, rather than of fat, this is particularly useful in the fattening of pigs. The feed additives of the present invention are useful in the fattening of pigs, cattle and poultry. Thus 5-methyl-7-ethoxy-isoflavone induces a weight-gain of 9–10% on chicken during a fattening period of 5 weeks.

The following test-results show the useful anabolic properties of the compounds of the present invention.

(A) Test animals: broiler, cocks
Test period: 7 weeks.
Number of animals per group: 20
Concentration of test compounds: 2 g./100 kg fodder and 5 g./100 kg fodder.

| Group | Weight after 6 weeks in g. | Amount of fodder used for 1 kg. of body weight (in kg.) |
|---|---|---|
| Control | 1215 | 2.75 |
| Compound B (2 g./100 kg.) | 1360 | 2.57 |
| Compound B (5 g./100 kg.) | 1352 | 2.50 |

(B) Test animals sexed cocks:
Test period: 35 days
Number of animals pro group: 30
Concentration of test compound 2 g./100 kg. fodder.
In the first week of the pre-breeding period and the first week of the test period, the animals received a starter fodder, and in the further time of the test a breeding fodder. For 5–12 days the animals were given sulfaquinoxaline as a cocciodiostatic agent.

| Compound | Weight-gain increase in % related to the control |
|---|---|
| Compound A | + 8.70 |
| Compound B | + 6.24 |
| Compound C | + 4.33 |
| Compound D | + 3.70 |
| Control | 0.00 |

The following test compounds were used:
Compound A = 5-methyl-7-methoxy-isoflavone
Compound B = 5-methyl-7-ethoxy-isoflavone
Compound C = 5-methyl-7-(2-hydroxy-ethoxy)-isoflavone
Compound D = 5-methyl-7-isopropoxy-isoflavone.

The starter fodder was of the following composition: Maize 60%; soya (45%) 20%; lucerne meal 2%; fish meal (65%) 10%; yeast 3.3%; calcium phosphate 0.6%; lime 2.3%; sodium chloride 0.3%; vitamin premix I 1.0%; mineral premix I 0.5%.

The composition of the poultry breeding fodder is the following: maize 50%, wheat 14.9%; soya (45%) 12.5%; peanut 9%; lucerne meal 2.0%; fish meal (65%) 4.5%; meat meal (45%) 3.0%; calcium phosphate 1.0%; lime 1.8%; sodium chloride 0.3%; vitamin premix II 0.5%; mineral premix I 0.5%.

The vitamin premixes are of the following compositions:

| Compositions of vitamin premixes | Vitamin premix I 0.5% | Vitamin premix II 0.5% |
|---|---|---|
| A-vitamin | 2,000,000 IU | 1,200,000 IU |
| $D_3$-vitamin | 400,000 IU | 300,000 IU |
| E-vitamin | 4,000 IU | 2,000 IU |
| $K_3$-vitamin | 400 mg | 400 mg |
| $B_1$-vitamin | 400 mg | 200 mg |
| $B_2$-vitamin | 800 mg | 700 mg |
| $B_3$-vitamin | 1,200 mg | 2,000 mg |
| $B_6$-vitamin | 400 mg | 500 mg |
| $B_{12}$-vitamin | 10 mg | 4 mg |
| Niacine | 4,000 mg | 5,000 mg |
| Choline chloride | 100,000 mg | 100,000 mg |
| Ethoxy-methyl-quinoline | 25,000 mg | 25,000 mg |
| Bacitracin | 6,000 mg | 4,000 mg |
| Furazolidone | 20,000 mg | — |
| Ardinon | — | 25,000 mg |

| Compositions of mineral premix I | |
|---|---|
| Manganese | 20,000 mg |
| Iron | 2,000 mg |
| Zinc | 8,000 mg |
| Copper | 400 mg |
| Iodine | 150 mg |
| Ethoxy-methyl-quinoline | 100 mg |
| mixed in 100,00 g. of bran. | |

The feed additives compounds of the formula I are added to the fodder preferably in an amount of 0.0001–0.1%. A preferred active ingredient content is 0.5–5 g./100 kg. fodder, particularly 2 g./100 kg. fodder. The active ingredient content of the fodder may be, however, higher or lower, than the above values.

The compounds of the formula I may be mixed with further additives. Substances with biological activity, such as vitamins, amino acids, choline chloride, salts of mineral acids, trace elements and other known substances of biological importance are suitable. The feed additive can be applied in premixes, in admixture with other components possessing biological effect. As further additives various diluents, solvents, sliding and molding substances and carriers may be used. The feed additive can be mixed to the feed as a powder, granulate, powder mixture, emulsion or suspension. It is also possible to use the feed composition in mixtures added to the drinking water of the animals.

Further details of our invention are to be found in the examples, without limiting the scope of our invention to the examples.

EXAMPLE 1

A mixture of 25 g. of 2,4-dihydroxy-6-methyl-phenyl-benzyl-ketone, 5 ml. of morpholine, 25 ml. of triethyl-orthoformiate and 100 ml. of dimethylformamide is refluxed under a fractionating column. The alcohol formed is distilled off. After the distillation of alcohol has ceased, the reaction mixture is heated to boiling for a further period of 30 minutes. The mixture is diluted with water, the precipitated product is filtered off and recrystallized from glacial acetic acid. The melting point of the 7-hydroxy-5-methyl-isoflavone thus obtained amounts to 241°–242° C.

EXAMPLE 2

25 g. of 2,4-dihydroxy-phenyl-benzyl-ketone are dissolved in 500 ml. of ether, 20 g. of zinc-cyanide are added and the solution is saturated with gaseous hydrogen chloride. After standing for 8 hours, the solvent is removed by decanting and the precipitated product is heated to boiling with water for an hour. The precipitated product is filtered off and recrystallized from glacial acetic acid. The 5-methyl-7-hydroxy-isoflavone thus obtained is identical with the product of Example 1.

EXAMPLE 3

A mixture of 13 g. of 5-methyl-7-hydroxy-isoflavone, 75 ml. of dried acetone, 13 g. of anhydrous potassium carbonate and 10.5 ml. of diethylsulphate is refluxed under stirring for 4 hours. Three quarters of the acetone is distilled off and to the residue water is added. The fluocculent product is filtered off recrystallized from methanol. The melting point of the 5-methyl-7ethoxy-isoflavone thus obtained amounts to 112°–114° C. The product froms colorless crystals.

The 5-methyl-7-methoxy-isoflavone is obtained in an analogous manner. Mp.: 117°–119° C.

EXAMPLE 4

13 g. of 5-methyl-7-hydroxy-isoflavone are dissolved in 70 ml. of dimethylformamide, whereupon 26 g. of powdered potassium carbonate and 20 ml. of isopropyl bromide are added and the reaction mixture is stirred at 80° C. for 6 hours. The mixture is cooled, poured into water, the precipitated crude product is filtered off and crystallized from methanol. The melting point of the 5-methyl-7-isopropoxy-isoflavone amounts to 94°–96° C. The product forms colorless needles.

In an analogous manner the following compound is prepared:
5-methyl-7-(2-hydroxy-ethoxy)-isoflavone, mp.: 135°–139° C.

EXAMPLE 5

1 g. of 5-methyl-7-ethoxy-isoflavone and a solution of 1 g. of sodium hydroxide in 20 ml. of 50% aqueous ethanol is heated to boiling for 2 hours. The reaction mixture is cooled, diluted with 20 ml. of water and neutralized with phosphonic acid. In the form of colorless crystals melting at 53.5° C., 2-hydroxy-4-ethoxy-phenyl-benzyl-ketone is obtained.

In an analogous manner the following compounds are prepared:

2-hydroxy-4-methoxy-phenyl-benzyl-ketone, mp.: 90° C.;
2-hydroxy-4-(2-hydroxy-ethoxy)-phenyl-benzyl-ketone, mp.: 117°–119° C.;
2-hydroxy-4-isopropoxy-phenyl-benzyl-ketone, mp.: 58.5°–59.5° C.;
2-hydroxy-4-(2-methyl-propoxy)-phenyl-benzyl-ketone, mp.: 57°–59° C.;
2-hydroxy-4-(3-methyl-butoxy)-phenyl-benzyl-ketone, mp.: 60°–61.5° C.

EXAMPLE 6

Formulation of poultry raising feed:

| | |
|---|---|
| Maize | 40.0 kg. |
| Feed wheat | 20.0 kg. |
| Bran | 6.0 kg. |
| Extracted Soyabeans | 13.0 kg. |
| Extracted groundnut | 11.5 kg. |
| Powdered alfalfa | 1.4 kg. |
| Extracted sunflower seed | 4.0 kg. |
| Potassium-phosphorus composite (Foszkal) | 0.5 kg. |
| Feed lime | 2.3 kg. |
| Feed sodium chloride | 0.3 kg. |
| Vitamin premix 2 | 0.5 kg. |
| Mineral Premix II | 0.5 kg. |
| Total: | 100.0 kg. |

+2 g. of 5-methyl-7-isopropoxy-isoflavone/100 kg. of feed.

EXAMPLE 7

A fodder of the following compositions is prepared for pigs:

| | |
|---|---|
| Bran | 22.0 kg. |
| Extracted soyabeans | 15.0 kg. |
| Extracted groundnut | 6.0 kg. |
| Powdered linseed | 14.0 kg. |
| Powdered alfalfa | 4.0 kg. |
| Powdered milk | 15.0 kg. |
| Fish meal | 10.0 kg. |
| Yeast | 2.0 kg. |
| Feed lime | 6.0 kg. |
| Feed sodium chloride | 1.5 kg. |
| Vitamin premix | 3.0 kg. |
| Mineral premix | 1.5 kg. |
| Total: | 100.0 kg. |

+2 g. of 5-methyl-7-isopropoxy-isoflavone/100 kg. of feed.

As active ingredient other anabolic compounds of the formula I may be used too.

EXAMPLE 8

A tablet suitable for oral administration to humans in the dosage indicated is pressed from the following composition:

| | |
|---|---|
| Active ingredient of the formula I | 0.100 g. |
| Potato starch | 0.084 g. |
| Magnesium stearate | 0.010 g. |
| Polyvinylpyrrolidine | 0.006 g. |
| Total: | 0.200 g. |

The tablets are stable at a temperature of 40°–55° C. and desintegration time is 6–8 minutes.

EXAMPLE 9

A tablet may be pressed from the following composition:

| | |
|---|---|
| Active ingredient of the formula I | 0.1 g. |
| Avicel (Encompress) | 0.1 g. |
| Total: | 0.2 g. |

Comparative test report

Test animals: one week old cocks of 110 g. in four groups containing 20 animals each

| Duration of the treatment (weeks) | Average weights (g) | | |
|---|---|---|---|
| | group 1 | group 2 | group 3 |
| 3 weeks | 440 | 443 | 446 |
| 4 weeks | 610 | 634 | 580 |
| 5 weeks | 842 | 867 | 742 |
| 6 weeks | 1013 | 1097 | 903 |
| 7 weeks | 1310 | 1360 | 1232 |
| Feedstuff per one kg. of live weight | 2.63 | 2.57 | 2.83 |

| | |
|---|---|
| For group 1: | 2 g. of 7-isopropoxy-isoflavone/q added to feedstuff |
| For group 2: | 2 g. of 5-methyl-7-isopropoxy-isoflavone/q added to feedstuff |
| For group 3: | 1 g. bacitracine/q added to feedstuff |

| | Increase in weight | Saving in feedstuff related to 1 kg. of live weight |
|---|---|---|
| 7-isopropoxy-isoflavone | 6.3% | 8% |
| 5-methyl-7-isopropoxy-isoflavone | 10.3% | 9.2% |

Comparative tests

The active compound was incorporated into poultry feed in a concentration of 2 g./100 kg. The test was carried out on broiler chickens which were fed with the feed from an age of 2 days of an age of 5 weeks. In each group 15 chickens were used.

The following test compounds were used:
Compound A = 5-methyl-7-methoxy-isoflavone,
Compound B = 5-methyl-7-ethoxy-isoflavone,
Compound C = 7-isopropoxy-isoflavone.

(i.) The test results are summarized in the following table:

| Test Compound | Weight increase in % |
|---|---|
| (A) | 8 |
| (B) | 8 |
| (C) | 4.5 |

The above results have a significance of p 0.01.

(ii.) The test was carried out as described in (i.) except that the animal groups consisted of 100 broiler chickens. The results are summarized in the following table:

| Compound | Weight in % |
|---|---|
| (B) | 10 |
| (C) | 4.8 |

We claim:

1. An anabolically effective compound for use as a pharmaceutical or a feed additive of the formula

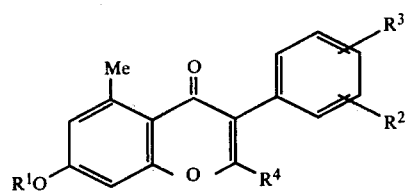

wherein R' is methyl, ethyl, isopropyl or hydroxyethyl; and $R^2$, $R^3$ and $R^4$ are hydrogen.

2. The compound defined in claim 1 which is: 5-methyl-7-methoxy-isoflavone.
3. The compound defined in claim 1 which is: 5-methyl-7-ethoxy-isoflavone.
4. The compound defined in claim 1 which is: 5-methyl-7-ixopropoxy-isoflavone.
5. The compound defined in claim 1 which is: 5-methyl-7-(2-hydroxy-ethoxy)-isoflavone.

* * * * *